(12) United States Patent
Song et al.

(10) Patent No.: US 11,666,448 B2
(45) Date of Patent: Jun. 6, 2023

(54) KNEE PROSTHESIS AND KNEE PROSTHESIS COMPONENT

(71) Applicants: BEIJING NATON MEDICAL TECHNOLOGY RESEARCH INSTITUTE CO. LTD., Beijing (CN); TIANJIN ZHENGTIAN MEDICAL INSTRUMENT CO., LTD., Tianjin (CN)

(72) Inventors: Dayong Song, Beijing (CN); Senyuan Hu, Beijing (CN); Jian Wang, Beijing (CN); Xiang Dong, Beijing (CN)

(73) Assignees: TIANJIN ZHENGTIAN MEDICAL INSTRUMENT CO., LTD., Tianjin (CN); BEIJING NATON MEDICAL TECHNOLOGY RESEARCH INSTITUTE CO., LTD., Beijing (CN)

( * ) Notice: Subject to any disclaimer, the term of this patent is extended or adjusted under 35 U.S.C. 154(b) by 123 days.

(21) Appl. No.: 16/745,821

(22) Filed: Jan. 17, 2020

(65) Prior Publication Data
US 2020/0229934 A1    Jul. 23, 2020

(30) Foreign Application Priority Data
Jan. 22, 2019    (CN) .......................... 201910059029.X (51) Int. Cl.
*A61F 2/38*    (2006.01)
*A61F 2/30*    (2006.01)

(52) U.S. Cl.
CPC ............ *A61F 2/3868* (2013.01); *A61F 2/389* (2013.01); *A61F 2/3859* (2013.01);
(Continued)

(58) Field of Classification Search
CPC .......... A61F 2/38; A61F 2/389; A61F 2/3868
See application file for complete search history.

(56) References Cited

U.S. PATENT DOCUMENTS 7,628,818 B2 * 12/2009 Hazebrouck ............ A61F 2/389
623/20.14
9,763,794 B2 * 9/2017 Sanford ................ A61F 2/3836
(Continued)

FOREIGN PATENT DOCUMENTS

FR          2 653 992 A1 *  5/1991  ............... A61F 2/38
WO      WO 2009/128943      10/2009
WO      WO 2020/011705 A1   1/2020

OTHER PUBLICATIONS

Extended European Search Report dated May 26, 2020 for Application No. 20152675.3, 8 pages.
(Continued)

*Primary Examiner* — David H Willse
(74) *Attorney, Agent, or Firm* — Frost Brown Todd LLP (57) ABSTRACT

A knee prosthesis includes a tibial component, a bearing and a femoral component. The tibial component includes a platform and at least one rib extending upwardly and forwardly, a front edge of upper surface of the platform is provided with at least one front lug boss, and back edge of the upper surface of the platform is provide with at least one back lug boss. The lower surface of the bearing is provided with a groove matching with the at least one rib, a front slot matching with the front lug boss and a back slot; the femoral component is articulated with the bearing; at least one rib is provided with a medial wall and a lateral wall, one of the them is provided with a bent portion and formed with a first inclined surface which extends in a direction away from the other one.

21 Claims, 7 Drawing Sheets

(52) U.S. Cl.
CPC ............... *A61F 2002/30116* (2013.01); *A61F 2002/30153* (2013.01); *A61F 2310/00029* (2013.01)

(56) References Cited

U.S. PATENT DOCUMENTS

| | | |
|---|---|---|
| 10,226,348 B2* | 3/2019 | Cappelletti .............. A61F 2/38 |
| 2009/0082873 A1 | 3/2009 | Hazebrouck et al. |
| 2010/0063594 A1 | 3/2010 | Hazebrouck et al. |
| 2013/0131816 A1 | 5/2013 | Parisi et al. |
| 2015/0173781 A1* | 6/2015 | Metzger ................ A61F 2/4657 |
| | | 606/88 |

OTHER PUBLICATIONS

European Office Action dated Dec. 16, 2022 for Application No. 20152675.3, 5 pages.

* cited by examiner

KNEE PROSTHESIS AND KNEE PROSTHESIS COMPONENT

CROSS REFERENCE

This application claims priority to Chinese Patent Application No. 201910059029.X, filed on Jan. 22, 2019, the entire contents of which are incorporated herein by reference.

TECHNICAL FIELD

The present disclosure relates to an implantable orthopedic prosthesis in general, and in particular, to a knee prosthesis and a knee prosthesis component.

BACKGROUND

The concept of knee prosthesis design is generally based on a same principle, that is, the implanted knee element provides a biomechanical motion pattern similar to a normal knee, and obtains static and dynamic stability by means of the balance between the implant itself and the ligament and the soft tissue of the knee. These knee element designs all attempt to restore the natural movement of human knee, and adjust and control the forces generated in the knee movement during flexing and stretching. However, all current knee prosthesis designs do not meet this standard.

The traditional knee prosthesis mainly includes a femoral component for combining with the femur, a tibial component for combining with the tibia, and a bearing provided on the upper surface of the tibial component. Where in the fixed-bearing knee prosthesis, after the bearing is disposed on the tibial component, the bearing can't slide relative to the tibial component.

In the related art, a fixing groove is usually formed along the edge contour or the central protrusion of the tibial component platform to guide or position, and an elastic latch and the fixing groove are provided at the front and the back of the bearing to achieve the purpose of locking.

However, during the use of the knee prosthesis, the direction of the stress is mainly relative to the front and back of the patient, so the forward shearing force of the bearing is greater than that of the left and right sides, as a result, the bearing will move forward slightly and be worn out due to the frequent relative sliding. The locking structure in the above related art is likely to cause stress concentration in the contact area between the bearing and the tibial edge contour, resulting in insufficient locking force to offset the shearing force of the forward movement of the bearing, thereby causing an increase in the micro-momentum and serious wear of the lower surface of the bearing.

The above information disclosed in the background section is only used to enhance the understanding of the background of the present disclosure, so it may include information that does not constitute related technology known to those of ordinary skill in the art.

SUMMARY

According to one aspect of the disclosure, a knee prosthesis is provided, which includes a tibial component, a bearing and a femoral component. The tibial component, comprises a platform and at least one rib extending upwardly from an upper surface of the platform and forwardly from the rear of the platform, a front edge of the upper surface of the platform is provided with at least one front lug boss, and a back edge of the upper surface of the platform is provided with at least one back lug boss; a lower surface of the bearing is provided with a groove matching with the at least one rib, and the bearing is provided with a front slot matching with the front lug boss and provided with a back slot matching with back lug boss; and the femoral component is articulated with an upper surface of the bearing; where, at least one of the ribs is provided with a medial wall and a lateral wall, at least one of the medial wall and the lateral wall is provided with a bent portion and formed with a first inclined surface; when there are at least two ribs, one of plurality of medial or lateral walls is provided with a bent portion and formed with a first inclined surface and the first inclined surface extends in a direction away from the other wall in the same rib.

According to one embodiment of the present disclosure, the first inclined surface and the upper surface of the platform form an intersection line, and an included angle ß between the intersection line and a central axis of the platform along a front-back direction is greater than 0 degree.

According to one embodiment of the present disclosure, the included angle ß ranges from 2 degrees to 70 degrees.

According to one embodiment of the present disclosure, the knee prosthesis further includes a pair of ribs wherein the pair of ribs are disposed at the middle of the upper surface of the platform, at least one of the pair of ribs is parallel or at an angle of greater than 0 relative to a central axis of the platform along a front-back direction.

According to one embodiment of the present disclosure, the bent portion is provided with a notch, and the notch extends upward from the upper surface of the platform and terminates at an upper surface of the rib.

According to one embodiment of the present disclosure, the tibial component includes a platform and at least one rib extending upwardly from an upper surface of the platform and forwardly from the rear of the platform, a front edge of the upper surface of the platform is provided with at least one front lug boss, and a back edge of the upper surface of the platform is provided with at least one back lug boss; a lower surface of the bearing is provided with a groove matching with the at least one rib, and the bearing is provided with a front slot matching with the front lug boss and a back slot matching with back lug boss; and the femoral component articulated with an upper surface of the bearing; wherein the at least one rib is provided with a medial wall and a lateral wall, wherein at least one of the medial wall and the lateral wall is provided with a bent portion and formed with a first inclined surface and the other wall of the same rib is not provided with a bent portion; the first inclined surface extends in a direction away from the other wall of same rib, in one embodiment, the first inclined surface and the upper surface of the platform form an intersection line, an included angle between the intersection line and a central axis of the platform along a front-back direction is greater than 0 degree, for example, the included angle ranges from 2 degrees to 70 degrees; or the other wall of the same rib is provided with a bent portion in a forward or a backward extending direction and it is formed with a second inclined surface, and wherein the second inclined surface and the first inclined surface are either parallel or angled relative to each other.

According to one embodiment of the present disclosure, the at least one rib and the grooves are interference fit in a width direction of the groove.

According to one embodiment of the present disclosure, the front lug boss is provided with at least one front undercut, the back lug boss is provided with at least one back undercut, and the lower surface of the bearing is provided with at least one front projection snapped into the front undercut and at least one back projection snapped into the back undercut.

According to one embodiment of the present disclosure, the at least one back undercut is located in the middle of a back edge of the platform.

According to another aspect of the present disclosure, a knee prosthesis component is provided, which includes one or more tibial components described above, and a plurality of bearings described above. Each of the bearings has a different width in a medial-lateral direction; the femoral components are articulated with an upper surface of the bearing.

BRIEF DESCRIPTION OF THE DRAWINGS

The above and other features and advantages of the present disclosure will become more apparent by describing the example embodiments in detail with reference to the accompanying drawings.

DETAILED DESCRIPTION

Example embodiments will now be described more fully with reference to the accompanying drawings. However, the exemplary embodiments can be implemented in various forms and should not be construed as limited to the embodiments set forth herein; rather, these embodiments are provided so that this disclosure will be thorough and complete, and will fully convey the concept of example embodiments to those skilled in the art. The same reference numerals in the drawings denote the same or similar structures, and thus their detailed descriptions will be omitted.

Figure 2:
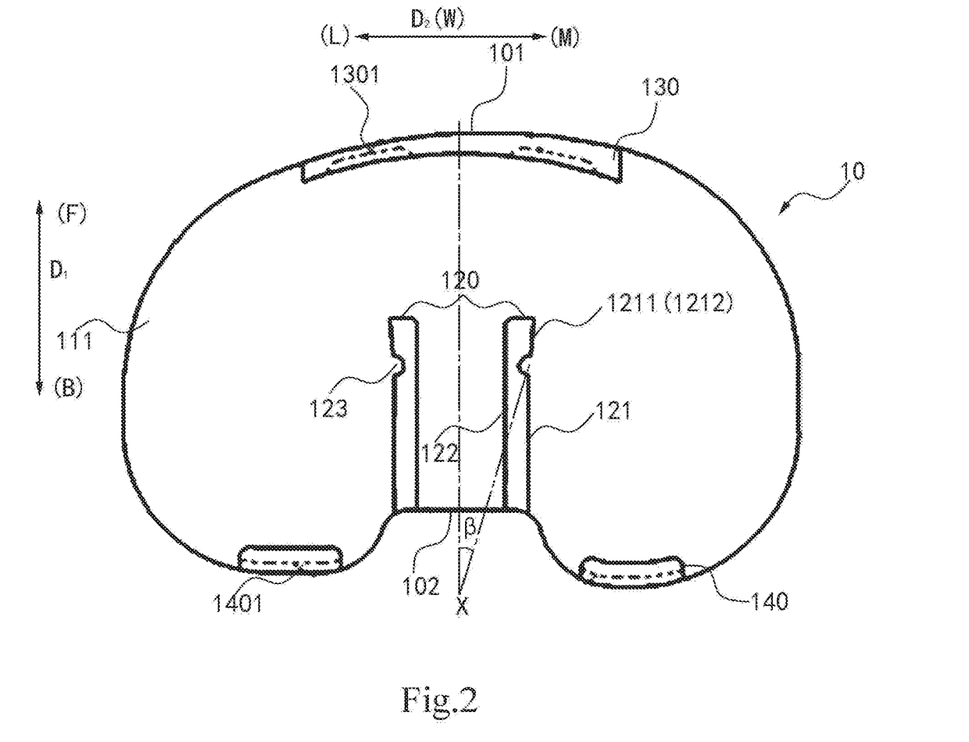
FIG. 2 is a top view showing a tibial component according to an exemplary embodiment.

In the present disclosure, the directions such as "front", "back" "up", "down", "medial" and "lateral" are respectively consistent with the "front", "back", "up", "down", "medial" and "lateral" directions of a knee prosthesis in the situation of a person standing after the knee prosthesis is implanted in the human body, and the present disclosure is described by taking the knee prosthesis of the left knee as an example, for example, as shown in FIG. 2, the right side of the tibial component is medial, and the left side of the tibial component is lateral, the upper side of the tibial component is front, and the lower side of the tibial component is back. As the arrows shown in FIG. 2, M indicates a medial (inward) direction, L indicates a lateral (outward) direction, F indicates a front direction and B indicates a back direction.

In the following, some embodiments of the present disclosure will be described in detail with reference to the drawings. In the case of no conflict, the features in the following embodiments can be combined with each other.

Figure 1:
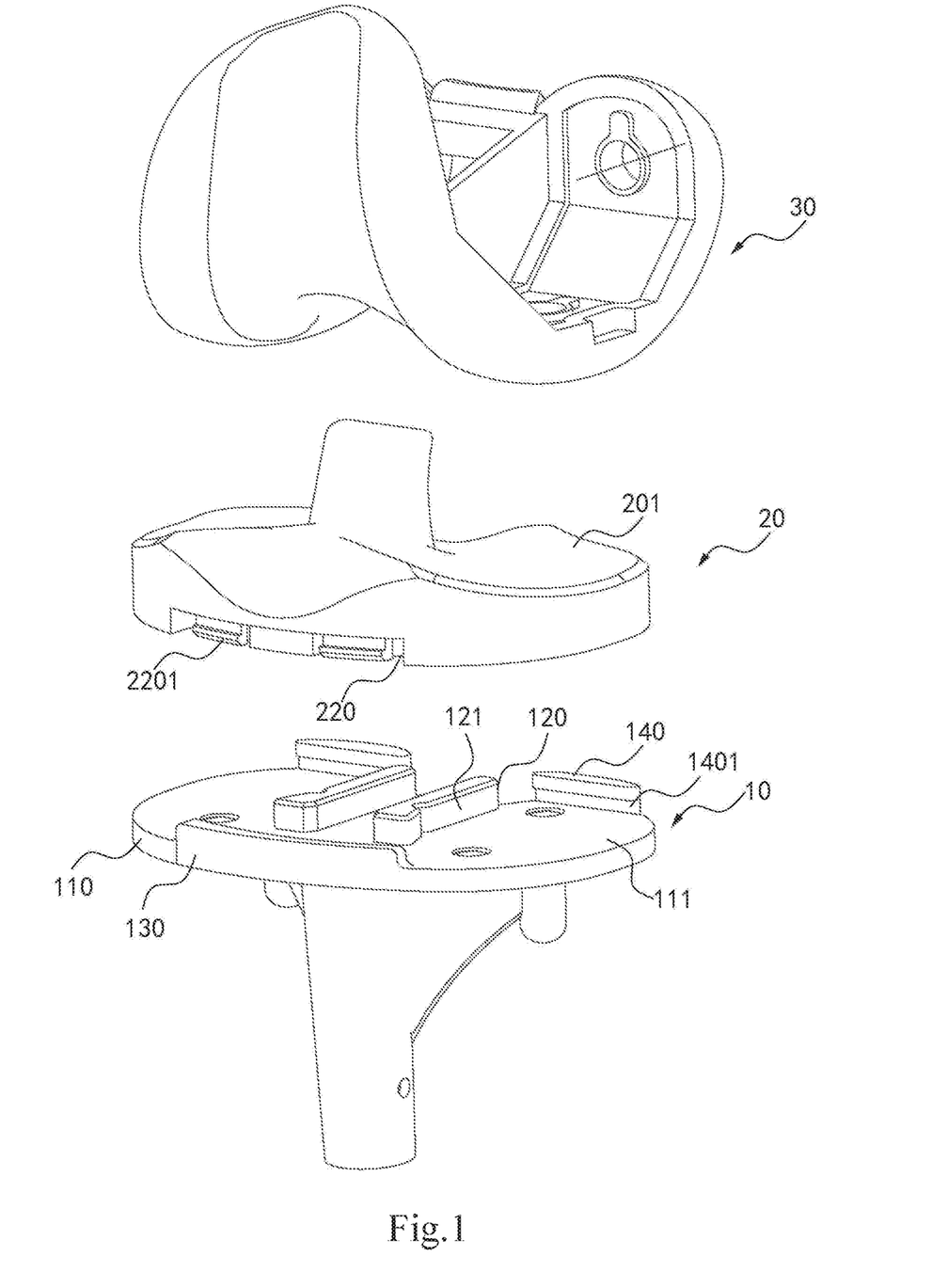
FIG. 1 is an exploded view showing a knee prosthesis according to an exemplary embodiment.
Figure 3:
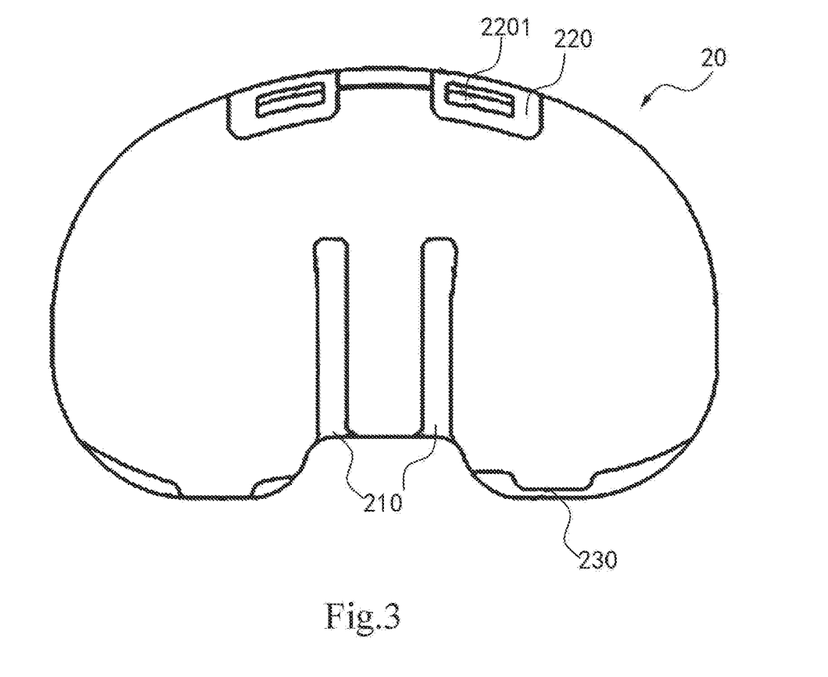
FIG. 3 is a bottom view showing a bearing according to an exemplary embodiment.
Figure 4:
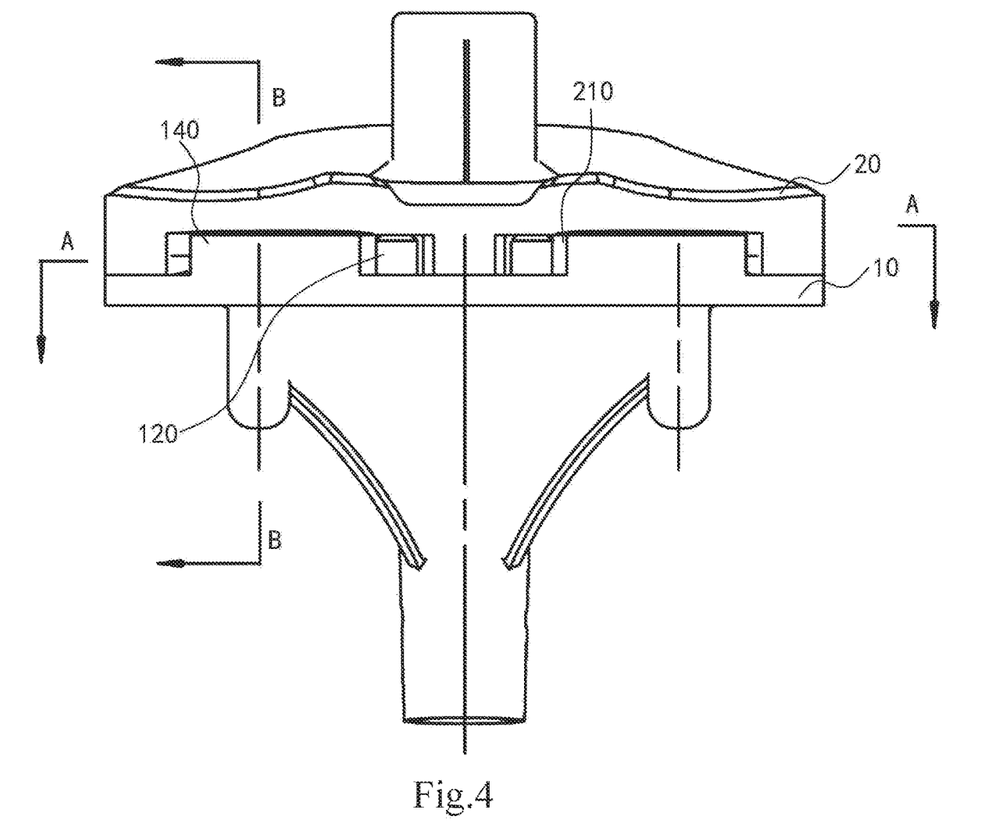
FIG. 4 is a rear view showing an assembly of a tibial component and a bearing according to an exemplary embodiment.
Figure 5:
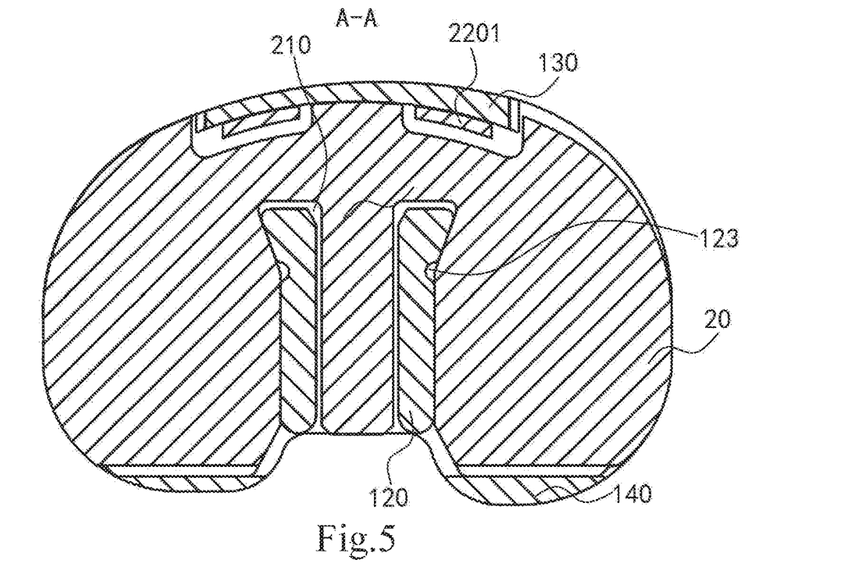
FIG. 5 is a cross-sectional view taken along the line A-A in FIG. 4.
Figure 6:
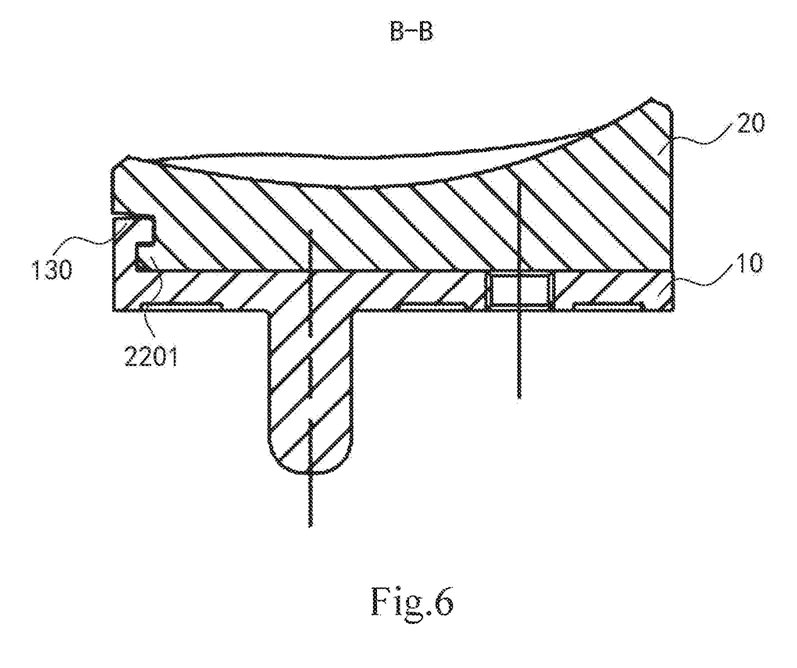
FIG. 6 is a cross-sectional view taken along the line B-B in FIG. 4.
Figure 7:
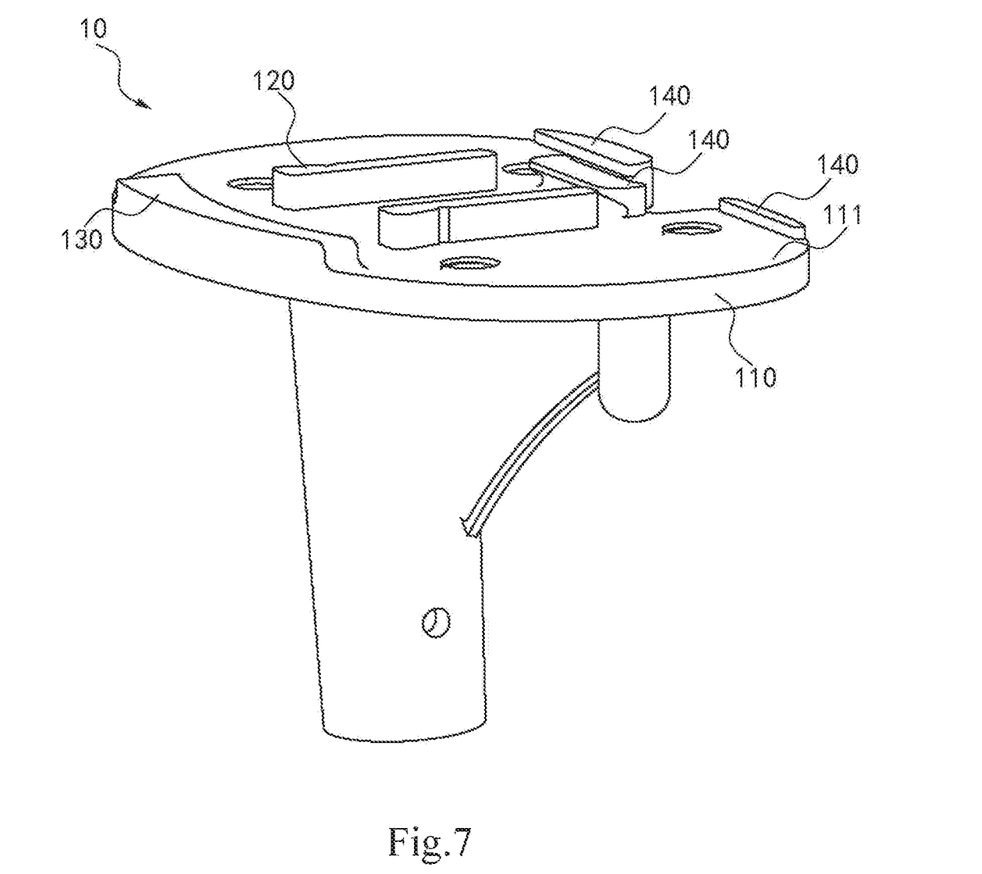
FIG. 7 is a perspective view showing a tibial component according to another exemplary embodiment.
Figure 8:
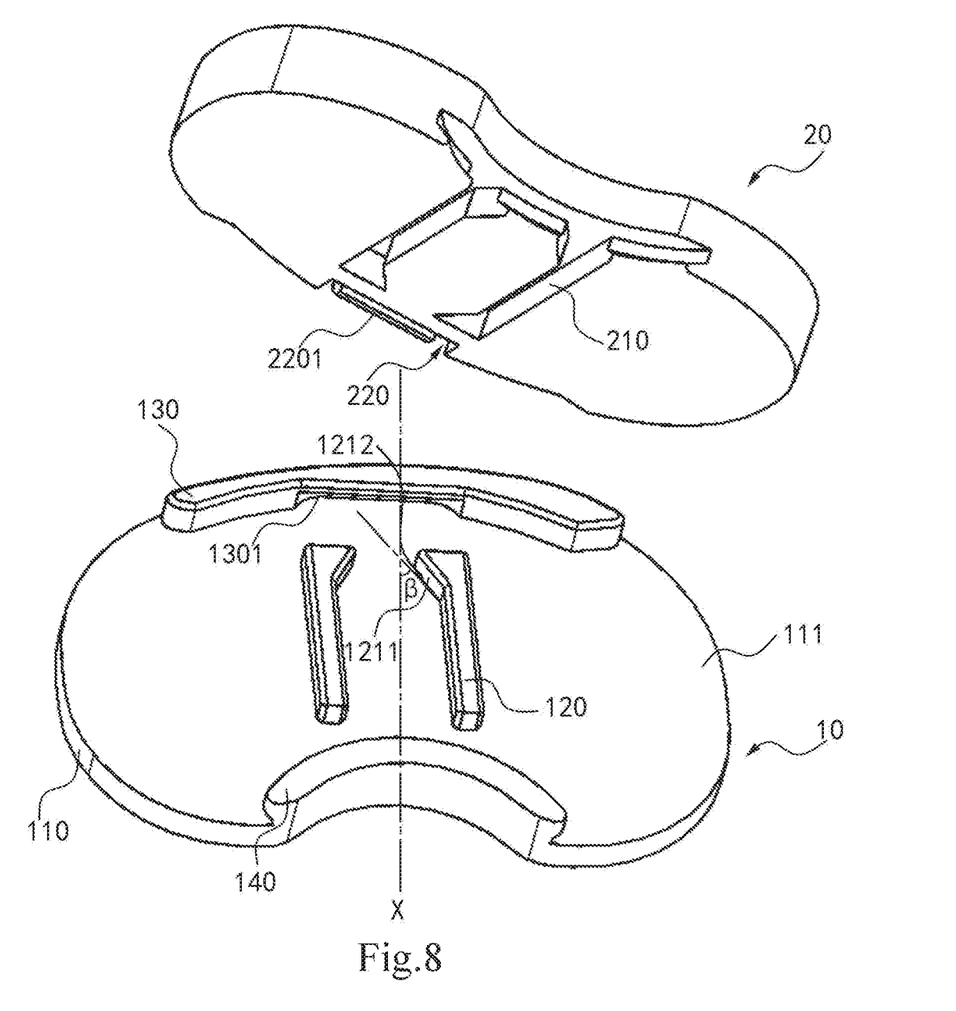
FIG. 8 is a perspective view showing a tibial component according to another exemplary embodiment.
Figure 9:
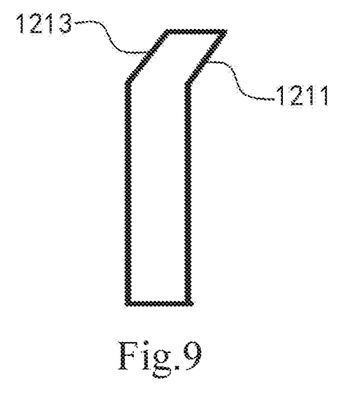
FIG. 9 is a schematic diagram showing a shape of a rib of a tibial component according to an exemplary embodiment.
Figure 10:
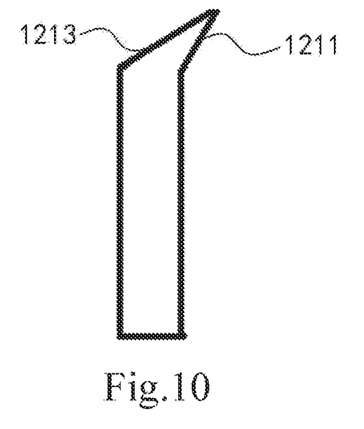
FIG. 10 is a schematic diagram showing a shape of a rib of a tibial component according to another exemplary embodiment.
Figure 11:
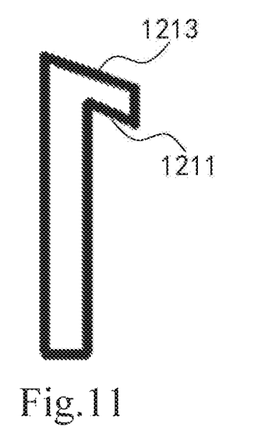
FIG. 11 is a schematic diagram showing a shape of a rib of a tibial component according to a further embodiment.

FIG. 1 is an exploded view showing a knee prosthesis according to an exemplary embodiment. FIG. 2 is a top view showing a tibial component according to an exemplary embodiment. FIG. 3 is a bottom view showing a bearing according to an exemplary embodiment. FIG. 4 is a rear view showing an assembly of a tibial component and a bearing according to an exemplary embodiment. FIG. 5 is a cross-sectional view taken along the line A-A in FIG. 4. FIG. 6 is a cross-sectional view taken along the line B-B in FIG. 4. FIG. 7 is a perspective view showing a tibial component according to another exemplary embodiment. FIG. 8 is a perspective view showing a tibial component according to a further embodiment. FIGS. 9 to 11 are schematic diagrams showing different shapes of ribs of tibial components according to exemplary embodiments.

As shown in FIG. 1, the present disclosure provides a knee prosthesis, which includes a tibial component 10, a bearing 20, and a femoral component 30. In one embodiment, the tibial component 10 includes a platform 110 and a fixing component located on the lower surface of the platform 110 and extending downward, such as an elongated rod, which can be implanted into the tibia of a patient by surgery (not shown). The bearing 20 may be fixed on the upper surface of the tibial component 10, such as the cooperation between the ribs 120 and the grooves 210 as described below. The femoral component 30 can be implanted into the femur of a patient by surgery (not shown), and configured to follow the natural femoral condyle configuration of the patient. The upper surface 201 of the bearing 20 includes a lateral support surface and a medial support surface, which are respectively articulated to the lateral condyle surface and the medial condyle surface of the femoral component 30. Of course, as is well known to those skilled in the art, patella components may also be included, which will not be described in detail here.

The tibial component 10 and the femoral component 30 may be made of a metal such as a cobalt chromium alloy, of course, other materials commonly used in the art may also be used. The bone-engaging surfaces of the tibial component 10 and the femoral component 30 can be textured to facilitate the bonding with the bone. In addition, these bone-engaging surfaces may also have a porous coating to promote bone endogenesis and thus permanently fix to the bone.

The bearing 20 may be made of a polymeric material, such as ultra-high molecular weight polyethylene (UHMWPE), but is not limited thereto.

The structures of the tibial component 10 and the bearing 20 will be described in detail below with reference to the drawings.

As shown in FIGS. 1, 2 and 3, the tibial component 10 includes a platform 110 and one or more ribs 120 extending upwardly from an upper surface 111 of the platform 110 and forwardly from a back edge 102 of the platform 110. The rib 120 may be integrally formed with the platform 110, for example, by milling. The size of the platform 110 may be in accordance with the shape of the patient's tibia after the top portion is surgically cut off, so that the lower surface of the platform 110 better matches the cross section of the tibia of the patient.

In other embodiments of the present disclosure, as shown in FIGS. 7 and 8, one or more ribs 120 start at the back of the platform 110 and extend forward, and are not connected to the back edge 102 of the platform 110, as long as it can play a role in guiding and positioning.

The number of the ribs 120 may be one, two or more. In one embodiment, at least one of the ribs 120 has a medial wall 121 and a lateral wall 122, in a direction which the ribs 120 extend forward, one of the medial walls 121 or the lateral wall 122 has a bent portion and forms a first inclined surface 1211, the first inclined surface 1211 extends in a direction away from the other wall of the same rib. The lower surface of the bearing 20 has a groove 210 matching the rib 120.

Figure 12:
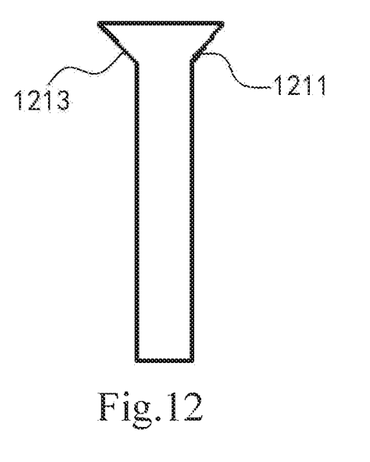
FIG. 12 is a schematic diagram showing a shape of a rib of a tibial component according to a further embodiment.

Specifically, in order to facilitate the following description, take the medial wall 121 with a bent portion as an example. As the right rib shown in FIG. 2, the medial wall 121 extends forward and inward to form a first inclined surface 1211, and the first inclined surface 1211 forms an angle with the rest of the medial wall 121. The first inclined surface 1211 is inclined inward in a forward extending direction, that is, away from the lateral wall 122. It should be noted that the "away from the other wall" in the present disclosure is away from a non-bent portion of the other wall of the same rib, if the other wall also has a bent portion in a forward extending direction and form the second inclined surface, when the first and the second inclined surface have the same bending direction (inward or outward), the first and the second inclined surface may be parallel or intersect shown in FIGS. 9 to 10. If two walls have the bent portions in a backward extending direction, the first and the second inclined surface form a shape shown in FIG. 11. In other words, if the other wall (the medial wall or the lateral wall) has a bent portion, the present disclosure does not specifically limit the bending direction of the bent portion, the bending direction may extend lateral or medial. When the first and the second inclined surface have the different bending direction, the width of rib gradually increases, as shown in FIG. 12. It should be understood that the above-mentioned various modifications are all within the protection scope of the present disclosure.

In addition, the front edge 101 of the upper surface 111 of the platform 110 is provided with at least one front lug boss 130, the back edge 102 of the upper surface 111 of the platform 110 is provided with at least one back lug boss 140. Accordingly, the bearing 20 has a front slot 220 matching the front lug boss 130 and a back slot 230 matching the back lug boss 140. When the bearing 20 is fixedly mounted on the upper surface 111 of the platform 110 of the tibial component 10, the front lug boss 130 may be fitted with the front slot 220, and the back lug boss 140 may be fitted with the back slot 230.

In the present disclosure, it is not limited whether the medial wall 121 and the lateral wall 122 of the rib 120 are inclined in the up-down direction.

During the use of the knee prosthesis, since the force direction of the patient's knee joint during flexion and extension is mainly relative to the patient's front-back direction D1, the forward shearing force of the bearing 20 is greater than the medial and the lateral, as a result, the bearing 20 will move forward slightly and be worn due to frequent relative sliding. The knee prosthesis provided by the present disclosure has a structural design of "one of the medial walls 121 or the lateral walls 122 of the ribs 120 has a bent portion and forms a first inclined surface 1211, and the first inclined surface 1211 extends in a direction away from the other wall of same rib", so that the medial wall 121 and/or the lateral wall 122 of the rib 120 have a inclined surface, the groove 210 also has an inclined surface at a corresponding position. Because the rib and the groove form an inclined surface fit, when the bearing is subjected a forward shearing force, the fit is gap free, The rib 120 effectively prevents the bearing 20 from moving forward, and significantly reduces the occurrence of micro movement between the bearing 20 and the tibial component 10. At the same time, according to the principle of trigonometric function, the inclined surface of the rib 120 will decompose the forward force of the bearing 20 into a part of the force in a non-forward direction, effectively reducing the forward shearing force of the bearing 20 and reducing the tendency of the bearing 20 to slide forward. According to this, the inclined surface fit of the rib 120 and the groove 210 effectively hinders the forward sliding of the bearing 20, reduces the micro-momentum of the bearing 20, and effectively reduces the wear of the lower surface of the bearing 20.

Please continue to refer to FIGS. 1 to 3 and 8. In an embodiment of the present disclosure, the first inclined surface 1211 and the upper surface 111 of the platform 110 form an intersection line 1212, and an included angle ß between the intersection line 1212 and the central axis X of the platform 110 along the front-back direction D1 is greater than 0 degree. For example, as shown in FIGS. 1 to 11, the included angle ß may be 0 degrees to 90 degrees, and in one embodiment, the included angle ß may be 2 degrees to 70 degrees. In addition, as with the shape shown in FIG. 11 the included angle may also be 90 degrees to 180 degrees.

Please continue to refer to FIGS. 1 to 3. In an embodiment of the present disclosure, there are a pair of the ribs 120 disposed at the middle of the upper surface 111 of the platform 110. The arrangement of the two ribs 120 makes the reaction force given to the bearing 20 by the ribs 120 more uniform, stable, and powerful.

In other embodiments, the pair of ribs 120 may be disposed axially symmetrically with the center axis X of the platform 110 along the front-back direction D1.

It should be understood that the two ribs 120 described above may have substantially the same height, or may have different heights. Among them, the term "approximately" means covering any minor change. There will be errors in measurement and assembly, but this kind of error will not change its essence.

In one embodiment, the ribs 120 may be parallel to the central axis X of the platform 110 along the front-back direction D1, and the rib 120 may also be at an angle to the central axis X of the platform 110 along the front-back direction D1, for example, an acute angle. Of course, the two ribs 120 may be parallel to the central axis X or may be at an angle with the central axis X, as long as the ribs can play a guiding role in the process of installing the prosthesis.

Please refer to FIGS. 4 to 6. In an embodiment of the present disclosure, the bent portion of the rib 120 has a notch 123, and the notch 123 extends upward from the upper surface 111 of the platform 110 and terminates at the upper surface of the rib 120. The function of the notch 123 is to prevent the sharp corner of the corresponding position of the groove 210 from interfering with the bent portion of the rib 120 when the rib 120 is assembled with the groove 210.

In the present disclosure, the specific shape of the notch 123 is not particularly limited. For example, the cross-sectional of the notch 123 may be semicircular, rectangular, or other shapes that allow the sharp corner of the groove 210 to be embedded in the notch 123 without interfering therewith.

As shown in FIG. 2 or FIG. 8, in an embodiment of the present disclosure, the medial wall 121 or the lateral wall 122 of the rib 120 may not have the above-mentioned bent portion, in other words, when the wall of the rib has the bent portion, the other wall of the rib 120 may be linearly extended from the back edge 102 of the platform 110 to the front edge 101.

In one embodiment, as shown in FIG. 8, the pair of ribs 120 are disposed axially symmetrically with the center axis X of the platform 110 along the front-back direction D1. The medial wall of the lateral rib (the left rib as shown in FIG. 8) has a bent portion and forms a first inclined surface which extends in a direction away from the lateral wall of the lateral rib, the lateral wall of the medial rib (the right rib as shown in FIG. 8) also has a bent portion and forms a first inclined surface 1211 which extends in a direction away from the medial wall of the medial rib, then the first inclined surface of the lateral rib and the first inclined surface 1211 of the medial rib are disposed axially symmetrically with the center axis X of the platform 110.

In another embodiment of the present disclosure, the other wall of the rib 120 has a bent portion in the forward extending direction and forms a second inclined surface 1213, the second inclined surface 1213 and the first inclined surface 1211 may be parallel or angled. Specifically, taking the extending direction of the first inclined surface 1211 shown in FIG. 2 as an example, the extending direction of the second inclined surface 1213 is described. In FIG. 2, the first inclined surface 1211 of the right rib extends forward and inward, and the second inclined surface 1213 may be parallel to the first inclined surface 1211, as shown in FIG. 9, the second inclined surface 1213 extends forward and inward, as shown in FIG. 10. Of course, the second inclined surface 1213 may also extend forward and outward, as shown in FIG. 12.

In one embodiment, the second inclined surface 1213 and the first inclined surface 1211 may be symmetrically arranged along the central axis of the ribs 120 along the front-back direction D1. According to this, when the bearing 20 is fixed to the tibial component 10, each rib 120 and each groove 210 respectively has two symmetrically arranged inclined mating surfaces, which more effectively hinders the forward movement of the bearing 20 and reduces the wear of the lower surface of the bearing 20.

In one embodiment of the present disclosure, the ribs 120 and the grooves 210 may be interference fit in the medial-lateral extending direction to prevent shaking caused by gaps in the medial-lateral extending direction.

In one embodiment of the present disclosure, the front lug boss 130 is provided with at least one front undercut 1301, the back lug boss 140 is provided with at least one back undercut 1401, as shown in FIGS. 5 to 8, and the lower surface of the bearing 20 is provided with one front projection 2201 snapped into the front undercut 1301 and at least one back projection snapped into the back undercut 1401.

According to this, the coordination between the ribs 120 and the grooves 210 can effectively prevent the bearing 20 from moving in the front/back direction and medial/lateral direction relative to the tibial component 10, the coordination between the front undercut 1301 and the front projection 2201 and the coordination between the back undercut 1401 and the back projection can effectively prevent the bearing 20 from moving in an upward direction relative to the tibial component 10.

The ribs 120 extend from the back to the front, during the installation process of the bearing 20, the ribs 120 play a role in alignment and guiding, so that the groove 210 of the bearing 20 accurately is caused to slide accurately along the rib 120 toward the back edge 102. Specifically, the user can first align the groove 210 with the rib 120, and then slide the groove 210 backward along the rib 120 until the back projection snaps into the back undercut 1401, and finally press the front of the bearing 20 downward so that the rib 120 is completely fitted with the groove 210, and at the same time, the front projection 2201 snaps into the front undercut 1301. According to this, the bearing 20 is completely fixed to the tibial component 10, and the locking in the front/back direction, the medial/lateral direction and the up-down direction is achieved.

In one embodiment of the present disclosure, the above described at least one back undercut 1401 is disposed at a middle portion of the back edge 102 of the platform 110. For example, as shown in FIG. 7, the back edge 102 of the platform 110 is provided with three back lug bosses 140, among them, the back lug boss 140 located in the middle of the back edge 102 has a back undercut 1401, and the remaining two back lug bosses 140 may without back undercut 1401. Correspondingly, the back edge of the lower surface of the bearing 20 is provided with three back slots 230 respectively matching the three back lug bosses 140, among them, the back slot 230 located in the middle has a back projection matching the back undercut 1401, and the remaining two back slots 230 may not have back projection.

The present disclosure also provides a knee prosthesis component, which includes one or more tibial components 10 of any one of the embodiments described above, a plurality of bearings 20 of any one of the embodiments described above, and a plurality of femoral components 30, connection relationship among the three is the same as the above, which is not repeated here, and the widths of the plurality of bearings 20 in the medial-lateral direction D2 are different.

The design of knee prostheses is usually commercially available in various sizes, especially in different widths, in order to adapt to the different body shapes and bones of patients in different groups. Based on this, the knee prosthesis component provided by the present disclosure fully considers the size flexibility of the tibial component 10 and the bearing 20.

Specifically, although the width of each bearing 20 may be different in the medial-lateral direction, the positions and shapes of the ribs 120 and the front and back lug bosses and undercuts of each tibial component 10 and the positions and shapes of the grooves 210 and the front and back slots and projections of each bearing 20 are unchanged. Therefore, the matching relationship between the groove 210 of the bearing 20 and the rib 120 is unchanged. Accordingly, a plurality of bearings 20 with different widths can be fixed to the tibial component 10 with the same size, which provides a surgeon with greater freedom in selecting different sizes of prosthetic components before and during surgery.

As previously mentioned, various designs of the knee prosthesis and knee prosthesis component provided by the present disclosure allow improving the interchangeability of different size prostheses. Specifically, any one of a plurality of bearings 20 having different widths can be fixed to tibial component 10 with one size, and this interchangeability can allow the reserve of the tibial component 10 to be reduced in the knee prosthesis component reserve, and also allow the selection of a bearing 20 with a suitable size after the tibial component 10 is implanted intraoperatively.

It should be understood that the present disclosure does not limit its application to the detailed structure and arrangement of the components proposed in this specification. The disclosure is capable of other embodiments and being practiced and carried out in various ways. The aforementioned variations and modifications fall within the scope of the present disclosure. It should be understood that the technical solutions disclosed and defined in this specification may be extended to all alternative combinations of two or more separate features mentioned or shown in the text and/or the drawings. All of these different combinations constitute various alternative technical solutions of the disclosure. The embodiments described in this specification illustrate the best modes known for carrying out the disclosure and will enable those skilled in the art to utilize the disclosure.

What is claimed is:

1. A knee prosthesis, comprising:
   a tibial component, comprises a platform and at least one rib extending upwardly from an upper surface of the platform and forwardly from a rear of the platform, a front edge of the upper surface of the platform is provided with at least one front lug boss, and a back edge of the upper surface of the platform is provided with at least one back lug boss;
   a bearing, a lower surface of the bearing is provided with a groove matching with the at least one rib, and the bearing is provided with a front slot matching with the at least one front lug boss and a back slot matching with the at least one back lug boss; and
   a femoral component, articulated with an upper surface of the bearing;
   wherein the at least one rib is provided with a medial wall and a lateral wall, wherein at least one of the medial wall and the lateral wall is provided with a bent portion and formed with a first inclined surface and the first inclined surface extends away from a non-bent portion of the other of the medial wall and the lateral wall of the same at least one rib in a direction from the back edge to the front edge;
   wherein the at least one rib is not connected to the back edge and is not connected to the front edge; and
   the bent portion is provided with a notch in rear of the first inclined surface, and the notch extends upward from the upper surface of the platform and terminates at an upper surface of the at least one rib.

2. The knee prosthesis according to claim 1, wherein the first inclined surface and the upper surface of the platform form an intersection line, and wherein an included angle between the intersection line and a central axis of the platform along a front-back direction is greater than 0 degrees.

3. The knee prosthesis according to claim 2, wherein the included angle ranges from 2 degrees to 70 degrees.

4. The knee prosthesis according to claim 3, further comprising a pair of the ribs disposed at the middle of the upper surface of the platform, wherein at least one of the ribs is parallel or at an angle relative to a central axis of the platform along a front-back direction.

5. The knee prosthesis according to claim 1, further comprising a pair of ribs wherein the pair of ribs are disposed at the middle of the upper surface of the platform, and at least one of the pair of ribs is parallel to a central axis of the platform along a front-back direction.

6. The knee prosthesis according to claim 1, further comprising a pair of ribs wherein the pair of ribs are disposed at the middle of the upper surface of the platform, and at least one of the pair of ribs is at an angle of greater than 0 relative to a central axis of the platform along a front-back direction.

7. The knee prosthesis according to claim 1, wherein the other of the medial wall and the lateral wall of the same at least one rib is not provided with a bent portion.

8. The knee prosthesis according to claim 1, wherein the other of the medial wall and the lateral wall of the same at least one rib is provided with a bent portion in a forward or a backward extending direction and it is formed with a second inclined surface, and wherein the second inclined surface and the first inclined surface are either parallel or angled relative to each other.

9. The knee prosthesis according to claim 1, wherein the at least one rib and the groove are interference fit in a width direction of the groove.

10. The knee prosthesis according to claim 1, wherein the at least one front lug boss is provided with at least one front undercut, the at least one back lug boss is provided with at least one back undercut, and the lower surface of the bearing is provided with at least one front projection snapped into the front undercut and at least one back projection snapped into the back undercut.

11. The knee prosthesis according to claim 10, wherein the at least one back undercut is located in the middle of a back edge of the platform.

12. The knee prosthesis according to claim 2, further comprising at least a pair of ribs and wherein the pair of ribs are disposed at the middle of the upper surface of the platform, at least one of the pair of ribs is parallel to a central axis of the platform along a front-back direction.

13. The knee prosthesis according to claim 2, further comprising a pair of ribs and wherein the pair of ribs are disposed at the middle of the upper surface of the platform and at least one of the pair of ribs is at an angle relative to a central axis of the platform along a front-back direction.

14. The knee prosthesis according to claim 2, wherein the other of the medial wall and the lateral wall of the same at least one rib is not provided with the bent portion.

15. The knee prosthesis according to claim 2, wherein other of the medial wall and the lateral wall of the same at least one rib is provided with a bent portion in a forward or backward extending direction and is formed with a second inclined surface with the second inclined surface and the first inclined surface being parallel or angled relative to each other.

16. The knee prosthesis according to claim 2, wherein the at least one rib and the groove are interference fit in a width direction of the groove.

17. The knee prosthesis according to claim 2, wherein the at least one front lug boss is provided with at least one front undercut, the at least one back lug boss is provided with at least one back undercut, and the lower surface of the bearing is provided with one front projection snapped into the front undercut and at least one back projection snapped into the back undercut.

18. A knee prosthesis component, comprising:
    one or more tibial components, wherein the one or more tibial component comprises a platform and a plurality of ribs extending upwardly from an upper surface of the platform and forwardly from a rear of the platform, a front edge of the upper surface of the platform is provided with at least one front lug boss, and a back edge of the upper surface of the platform is provided with at least one back lug boss;

a plurality of bearings, wherein a lower surface of each of the plurality of bearings is provided with a groove matching with one of the ribs, and each of the plurality of bearings is provided with a front slot matching with the at least one front lug boss and a back slot matching with the at least one back lug boss; each of the plurality of bearings has a different width in a medial-lateral direction; and a plurality of femoral components that are articulated with an upper surface of each of the plurality of bearings;

wherein at least one of the ribs is provided with a medial wall and a lateral wall, and at least one of the medial wall and the lateral wall is provided with a bent portion and formed with a first inclined surface, the first inclined surface extends away from a non-bent portion of the other of the medial wall and the lateral wall of the same at least one of the ribs in a direction from the back edge to the front edge;

wherein the at least one of the ribs is not connected to the back edge and is not connected to the front edge; and the bent portion is provided with a notch in rear of the first inclined surface, and the notch extends upward from the upper surface of the platform and terminates at an upper surface of the at least one rib.

19. The knee prosthesis component according to claim 18, wherein the first inclined surface and the upper surface of the platform form an intersection line and an included angle between the intersection line and a central axis of the platform along a front-back direction is greater than 0 degree.

20. The knee prosthesis component according to claim 19, wherein the included angle is 2 degrees to 70 degrees.

21. The knee prosthesis component according to claim 20, further comprising a pair of ribs wherein the pair of ribs are disposed at the middle of the upper surface of the platform, and at least one of the ribs is parallel or at an angle to a central axis of the platform along a front-back direction.

* * * * *